(12) United States Patent
Joskowicz et al.

(10) Patent No.: US 9,492,241 B2
(45) Date of Patent: Nov. 15, 2016

(54) IMAGE GUIDED ROBOTIC SYSTEM FOR KEYHOLE NEUROSURGERY

(75) Inventors: Leo Joskowicz, Jerusalem (IL); Moshe Shoham, Hoshaya (IL); Reuven Shamir, Haifa (IL); Moti Freiman, Petach Tikva (IL); Eli Zehavi, Haifa (IL); Yigal Shoshan, Ramat Raziel (IL)

(73) Assignee: Mazor Robotics Ltd., Caesarea (IL)

( * ) Notice: Subject to any disclaimer, the term of this patent is extended or adjusted under 35 U.S.C. 154(b) by 752 days.

(21) Appl. No.: 11/813,747

(22) PCT Filed: Jan. 12, 2006

(86) PCT No.: PCT/IL2006/000056
§ 371 (c)(1),
(2), (4) Date: Jul. 9, 2008

(87) PCT Pub. No.: WO2006/075331
PCT Pub. Date: Jul. 20, 2006

(65) Prior Publication Data
US 2009/0177081 A1    Jul. 9, 2009

Related U.S. Application Data

(60) Provisional application No. 60/643,427, filed on Jan. 13, 2005.

(51) Int. Cl.
*A61B 19/00* (2006.01)
*A61B 17/34* (2006.01)

(52) U.S. Cl.
CPC .............. *A61B 90/36* (2016.02); *A61B 34/20* (2016.02); *A61B 34/72* (2016.02); *A61B 90/11* (2016.02);
(Continued)

(58) Field of Classification Search
CPC combination set(s) only.
See application file for complete search history.

(56) References Cited

U.S. PATENT DOCUMENTS 5,383,454 A    1/1995   Bucholz
5,531,520 A *  7/1996   Grimson et al. .............. 382/131
(Continued)

FOREIGN PATENT DOCUMENTS

DE    100 29 737 A1    5/2003
EP      1 142 536 A1   10/2001
(Continued)

OTHER PUBLICATIONS

Kosugi, Y. et al., "An articulated neurosurgical navigation system using MRI and CT images", IEEE Trans. on Biomedical Eng. vol. 35(2), 1998, pp. 147-152.
(Continued)

*Primary Examiner* — Katherine Fernandez
*Assistant Examiner* — Farshad Negarestan
(74) *Attorney, Agent, or Firm* — Fish & Richardson P.C.

(57) ABSTRACT

A novel image-guided system for precise automatic targeting in minimally invasive keyhole neurosurgery. The system consists of a miniature robot fitted with a mechanical guide for needle, probe, or catheter insertion. Intraoperative, the robot is directly affixed to a head clamp or to the patient skull. It automatically positions itself with respect to predefined entry points and targets in a preoperative CT/MRI image following an anatomical registration with an intraoperative 3D surface scan of the patient facial features and a registration jig. The registration procedure is a novel three-way scheme, in which the intraoperative surface scan including the registration jig is matched to a model generated from the preoperative CT/MRI image, the robot position is known in relation to the registration jig, and the entry and target points are known from the preoperative CT/MRI image, such that the robot position can be related to the entry and target points.

31 Claims, 6 Drawing Sheets (52) U.S. Cl.
CPC ............... *A61B 90/13* (2016.02); *A61B 34/10* (2016.02); *A61B 90/361* (2016.02); *A61B 2017/3407* (2013.01); *A61B 2034/105* (2016.02); *A61B 2034/107* (2016.02); *A61B 2034/2055* (2016.02); *A61B 2034/2065* (2016.02); *A61B 2090/365* (2016.02); *A61B 2090/373* (2016.02)

(56) References Cited

U.S. PATENT DOCUMENTS

| | | | |
|---|---|---|---|
| 5,799,055 | A | 8/1998 | Peshkin et al. |
| 5,891,034 | A | 4/1999 | Bucholz |
| 6,198,794 | B1 | 3/2001 | Peshkin et al. |
| 6,226,548 | B1 | 5/2001 | Foley et al. |
| 6,301,495 | B1 | 10/2001 | Gueziec et al. |
| 6,837,892 | B2 | 1/2005 | Shoham et al. |
| 7,217,276 | B2 | 5/2007 | Henderson et al. |
| 7,280,710 | B1 * | 10/2007 | Castro-Pareja et al. ...... 382/303 |
| 2002/0038118 | A1 * | 3/2002 | Shoham ............................ 606/1 |
| 2002/0052709 | A1 * | 5/2002 | Akatsuka et al. ............ 702/153 |
| 2002/0091374 | A1 * | 7/2002 | Cooper ............................ 606/1 |
| 2002/0183608 | A1 | 12/2002 | Marmulla et al. |
| 2004/0116906 | A1 * | 6/2004 | Lipow ............................. 606/1 |
| 2004/0170315 | A1 * | 9/2004 | Kosaka et al. ................ 382/154 |

FOREIGN PATENT DOCUMENTS

| | | |
|---|---|---|
| WO | 03/105659 | 12/2003 |
| WO | 2004/100758 | 11/2004 |

OTHER PUBLICATIONS

Akatsuka, Y. et al., "AR navigation system for neurosurgery", Proc. of Medical Imaging and Computer-Aided Interventions, 2000, pp. 833-838.

Grimson, E. et al., "Clinical experience with a high precision image-guided neurosurgery system", Proc. of Medical Imaging and Computer-Aided Interventions, 1998, pp. 63-72.

W. A. Hall et al., Navigus trajectory guide, Neurosurgery, 46(2), pp. 502-504, 2000.

Chen, M.D. et al., "A robotics system for stereotactic neurosurgery and its clinical application", Proc. Conf. Robotics and Automation, 1998, pp. 995-1000.

Masamune, K. Ji, et al., "A newly developed stereotactic robot with detachable drive for neurosurgery", Proc. of Medical Imaging Computing and Computer Aided Imaging, 1998, pp. 215-222.

Davies, B. et al., "Neurobot: a special-purpose robot for neurosurgery", Proc. Int. Conf. on Robotics and Automation, 2000, pp. 410-414.

Hang, Q. et al., "The application of the NeuroMate Robot: a quantitative comparison with frameless and frame-based surgical localization systems", Computer Aided Surgery, vol. 7(2), 2002, pp. 90-98.

McBeth, P.B. et al., "Robotics in neurosurgery", The American Journal of Surgery vol. 188, pp. 68S-75S, 2004.

Tseng, C-S. et al., "Image guided robotic navigation system for neurosurgery," Journal of Robotic Systems, vol. 17, (2), 2000, pp. 439-447.

Chinzei, K. and Miller, K., "MRI Guided Surgical Robot", Australian Conf. on Robotics and Automation, Sydney, 2001.

Kansy, K. et al., "LOCALITE—a frameless neuronavigation system for interventional magnet resonance imaging", Proc. of Medical Image Computing and Computer Assisted Intervention, 2003, pp. 832-841.

Dorward, N.L. et al., "The advantages of frameless stereotactic biopsy over frame-based biopsy", British Journal of Neurosurgery, vol. 16(2), 2002.

Morgan, P.S. et al., "The application accuracy of the PathFinder neurosurgical robot", Computer Aided Radiology and Surgery, CARS'2003, Elsevier 2003.

Morgan, P.S. et al., "Improved accuracy of PathFinder Neurosurgical Robot", International symposium on Computer Aided Surgery around the Head, CAS-H'2004, 2004.

G. Taubin, "Estimating the tensor of curvature of a surface from a polyhedral approximations", ICCV, pp. 902-907, 1995.

Besl, P.J. et al., "A method for registration of #d shapes", IEEE Trans. on Pattern Analysis and Machine Intelligence, vol. 14(2), 1992.

Extended European Supplementary Search Report of the European Patent Office, in corresponding European patent application No. 06700656.9, dated Oct. 24, 2013.

* cited by examiner

IMAGE GUIDED ROBOTIC SYSTEM FOR KEYHOLE NEUROSURGERY

This application is the U.S. national phase of International Application No. PCT/IL2006/000056, filed Jan. 12, 2006, which claims priority from U.S. Provisional Application No. 60/643,427 filed Jan. 13, 2005. The disclosures of both applications are incorporated herein by reference in their entireties. The International Application published in English on Jul. 20, 2006 as WO 2006/075331 under PCT Article 21(2).

FIELD OF THE INVENTION

The present invention relates to the field of robot-aided surgery, especially for use in keyhole neurosurgical applications using a patient mounted miniature robot.

BACKGROUND OF THE INVENTION

Precise targeting of tumors, lesions, and anatomical structures with a probe, needle, catheter, or electrode inside the brain based on preoperative CT/MRI images is the standard of care in many keyhole neurosurgical procedures. The procedures include tumor biopsies, treatment of hydrocephalus, aspiration and evacuation of deep brain hematomas, Ommaya catheter insertion, Deep Brain Stimulation, and minimal access craniotomies, among others. In all cases, misplacement of the surgical instrument may result in non-diagnostic tissue or catheter misplacement, as well as hemorrhage and severe neurological complications. These minimally invasive procedures are difficult to perform without the help of support systems that enhance the accuracy and steadiness of the surgical gestures.

All of these procedures have four important common properties:
1) they are minimally invasive surgeries (MIS) performed via a keyhole of 3-30 mm diameter opened on the skull dura;
2) they require precise targeting and mechanical guidance support;
3) the targets and entry points are determined preoperatively in a CT/MRI image; and
4) it is assumed that little or no brain shift occurs due to the MIS approach.

All such minimally invasive keyhole neurosurgeries follow a similar protocol, both preopertively and intraoperatively, as shown in the following summary:
1. Preoperatively
  (a) Pre-imaging preparation: implant skull screws and/or attach skin markers
  (b) Image acquisition: acquire a CT/MRI image
  (c) Planning: elaborate the preoperative plan: identify targets and entry points
2. Intraoperatively
  (a) Preparation: set up the support system and make entry point incision
  (b) Localization: locate needle/probe at entry point and adjust orientation
  (c) Guidance: provide mechanical guidance for needle/probe insertion
  (d) Insertion: insert needle to planned depth at proper speed/force
  (e) Repeat steps (a)-(d) as necessary There are four main types of support systems currently in use in the execution of minimally invasive keyhole neurosurgery:

1. Stereotactic frames;
2. Navigation systems;
3. Robotic systems; and
4. Interventional imaging systems.

Each of these systems has comparative advantages and disadvantages, as generally perceived by those active in the field, with each system having its proponents and opponents. The following is a summary of these systems with a suggested list of the advantages and disadvantages of each:
1. Stereotactic frames, such as those supplied by Radionics Inc., of Burlington, Mass., USA, or as used in the Leksell Gamma Knife® supplied by Elekta AB of Stockholm, Sweden, provide precise positioning with a manually adjustable frame rigidly attached to the patient's skull. Prior to image acquisition, four frame position screws are implanted in the patient's skull. An imaging coordinate box is mounted on the frame and the patient is scanned with it. The surgeon identifies the brain targets and entry points on the images and computes the corresponding stereotactic frame coordinates. Intraoperatively, the stereotactic frame is adjusted according to the computed coordinates and mounted on the immobilized patient skull at the implanted screws. Keyhole surgery of the skull opening is then performed. Optionally, a linear drive needle insertion guide is mounted on the frame to automate needle insertion and retraction. The advantages of stereotactic frames are: 1) introduced in the 1970's, they are the current standard of care and are extensively used and clinically tested; 2) they are relatively accurate ($\leq 2$ mm of the target) and provide rigid support and guidance for needle insertion, and; 3) they are relatively inexpensive (USD 50K) as compared to other systems. Their generally perceived disadvantages are: 1) they require the preoperative implantation of the head screws under local anesthesia; 2) they may cause discomfort to the patient before and during surgery; 3) they are bulky, cumbersome, and require manual adjustment during surgery; 5) they require patient head immobilization during surgery; 6) selecting new target points during surgery requires new manual computations for frame coordinates; and 7) they do not provide real-time feedback and validation of the needle position.

2. Navigation systems such as those supplied by Medtronic Inc. of Minneapolis, Minn., USA and BrainLAB AG of Heimstetten, Germany, show in real time the location of hand-held tools on the preoperative image onto which targets have been defined. Such systems have been described in US Patent Application Publication No. 2002/0183608, assigned to BrainLAB, in U.S. Pat. Nos. 5,383,454 and 5,891,034 to R. D. Bucholz, and in numerous articles, such as those by Kosugi, Y. et al. "An articulated neurosurgical navigation system using MRI and CT images", IEEE Trans. on Biomedical Eng. Vol. 35 (2), 1998, pp 147-152; by Akatsuka, Y. et al. "AR navigation system for neurosurgery", Proc. of Medical Imaging and Computer-Aided Interventions, 2000, pp 833-838; and by Grimson, E, et al., "Clinical experience with a high precision image-guided neurosurgery system", Proc. of Medical Imaging and Computer-Aided Interventions, 1998, pp 63-72. The registration between the preoperative data and the patient is performed via skin markers affixed to the patient's skull before scanning, or by acquiring points on the patient's face with a laser probe or by direct contact. Augmented with a manually positioned tracked passive arm such as the EasyTaxis™ supplied by Phillips Inc., or the Navigus™ System supplied by Image-Guided Neurologics Inc, and as described in the article by W. A. Hall et al., Navigus trajectory guide, Neurosurgery, 46(2), pp. 502-4, 2000, they also provide mechanical guidance for targeting. Since nearly all navigation systems use optical tracking, careful camera positioning and maintenance of a direct line of sight between the camera and tracked instruments is required at all times. The main advantages of navigation systems are that: 1) they provide continuous, real-time surgical tool location information with respect to the defined target; 2) they allow the selection of new target points during surgery, and; 3) introduced in the 90's, they are gaining wide clinical acceptance. Their generally perceived disadvantages are: 1) their cost, which is of the order of USD 200K; 2) they require head immobilization or compensation for patient head movement by the use of dynamic referencing; 3) they require the maintenance of a line of sight; 4) they require manual passive arm positioning, which can be time-consuming and error-prone; and 5) they require intra-operative registration, whose accuracy depends on the positional stability of the skin.

3. Robotic systems provide frameless stereotaxy with a robotic arm that automatically positions itself with respect to a target defined in the preoperative image. Such systems for use in neurosurgery have been described in the articles by Chen, M. D., et al., "A robotics system for stereotactic neurosurgery and its clinical application", Proc. Conf. Robotics and Automation, 1998, pp 995-1000; by Masamune, K. Ji, et al., "A newly developed stereotactic robot with detachable drive for neurosurgery", Proc. of Medical Image Computing and Computer Aided Imaging, 1998, pp. 215-222, by Davies, B. et al., "Neurobot: a special-purpose robot for neurosurgery", Proc. Int. Conf. on Robotics and Automation}, 2000, pp 410-414; by Hang, Q. et al., "The application of the NeuroMate Robot: a quantitative comparison with frameless and frame-based surgical localization systems", Computer Aided Surgery, Vol. 7 (2), 2002, pp 90-98, and by McBeth, P. B. et al., "Robotics in neurosurgery", The American Journal of Surgery Vol. 188, pp. 68S-75S, 2004.

They have the potential to address intraoperative localization, guidance, and insertion (steps 2b, 2c, 2d in the summary list above) with a single system. The registration between the preoperative image and the intraoperative situation is done by direct contact or with video or X-ray images. Two floor-standing commercial robots include the NeuroMate™ supplied by Integrated Surgical Systems, USA and PathFinder™, supplied by Armstrong HealthCare Ltd, of the UK. Their advantages are that: 1) they provide a frameless integrated solution; 2) they allow for intraoperative plan adjustment; and 3) they are rigid and accurate. Their generally perceived disadvantages are that: 1) they are bulky and cumbersome due to their size and weight, and thus pose a potential safety risk; 2) they require head immobilization or real-time tracking, 3) they are costly (USD 300-500K), and 4) there are not commonly used, with only approximately a dozen systems currently deployed.

4. Interventional imaging systems produce images showing the actual needle/probe position with respect to the brain anatomy and target. Such systems are described in the articles by Tseng, C-S. et al., "Image guided robotic navigation system for neurosurgery", Journal of Robotic Systems, Vol. 17, (8), 2000, pp 439-447; by Chinzei, K and Miller. K., "MRI Guided Surgical Robot", Australian Conf. on Robotics and Automation}, Sydney, 2001; and by Kansy, K. et al. "LOCALITE—a frameless neuronavigation system for interventional magnetic resonance imaging", Proc. of Medical Image Computing and Computer Assisted Intervention, 2003, pp 832-841.

A few experimental systems also incorporate real-time tracking, such as is supplied by Stereotaxis, Inc., of St. Louis Mo., USA, and robotic positioning devices. The main advantage is that these systems provide real-time, up-to-date images that account for brain shift, and needle bending. Their main generally perceived drawbacks are: 1) limited availability; 2) cumbersome and time-consuming intraoperative image acquisition; 3) high nominal and operational costs, and 4) for intraoperative MRI, complete, expensive room shielding is required.

The comparative characteristics of these four prior art systems are summarized in Table 1, which shows a nominal rating scheme, based on generally accepted perception of the various support techniques for minimally invasive keyhole neurosurgery, though it is to be understood that different practitioners may consider somewhat different ratings for systems which they espouse. In this table, '+++' indicates the most advantageous, and '+' the least advantageous. Furthermore, the column heading abbreviations are for: 1) clinical accuracy, 2) range of applicability, 3) ease of use in the Operating Room, 4) intraoperative adaptability of preoperative plan, 5) bulk, including size and weight, 6) patient morbidity, and 7) system cost.

TABLE 1

| Method | Accuracy | Range | Ease of use | Adaptability | Bulk | Morbidity | Head fixation | Cost |
| --- | --- | --- | --- | --- | --- | --- | --- | --- |
| 1. Stereotactic frame | +++ | + | ++ | + | ++ | + | yes | +++ |
| 2. Navigation | ++ | ++ | +++ | ++ | + | ++ | yes | ++ |
| 3. Robotics | ++ | ++ | + | +++ | + | ++ | yes | + |
| 4. Interventional imaging | + | +++ | + | +++ | + | +++ | no | + |

To date, few clinical studies have been performed comparing the clinical accuracy of these systems. Frameless navigation has been compared with frame-based stereotaxy in the article by Dorward, N. L. et al., "The advantages of frameless stereotactic biopsy over frame-based biopsy", British Journal of Neurosurgery, Vol. 16 (2), 2002. Frameless robotics has been compared with frame-based stereotaxy in the articles by Hang, Q. et al., "The application of the NeuroMate Robot: a quantitative comparison with frameless and frame-based surgical localization systems", Computer Aided Surgery, Vol. 7 (2), 2002, pp 90-98; by Morgan, P. S. et al., "The application accuracy of the PathFinder neurosurgical robot", Computer Aided Radiology and Surgery, CARS'2003, Elsevier 2003; and by P. S. Morgan, et al., "Improved accuracy of PathFinder Neurosurgical Robot", International symposium on Computer Aided Surgery around the Head, CAS-H'2004, 2004.

In all cases, the desired Target Registration Error (TRE) is 1-2 mm, and is critically dependent, except for the interventional imaging systems, on the registration between the preoperative images and the intraoperative situation.

Referring again to Table 1, it is observed that existing support systems for precise targeting in minimally invasive keyhole neurosurgery system do not appear to provide a fully satisfactory solution for all such applications. Each of the methods has at least one characteristic which is significantly disadvantageous in comparison with the other methods, as shown by a single + sign. Thus, stereotactic frames entail patient morbidity, require head immobilization and manual adjustment of the frame, and do not allow intraoperative plan changes. Navigators are frameless but require line-of-sight between the position sensor and the tracked instruments and require time-consuming manual positioning of a mechanical guiding arm. Existing robotic systems can perform limited automatic targeting and mechanical guidance but are cumbersome, expensive and difficult to use, and require head immobilization. Interventional imaging systems do not incorporate preoperative planning, have limited availability, are time-consuming and incur high costs.

There therefore currently exists a need for an image-guided system for precise automatic targeting of structures inside the brain that is less disadvantageous overall than the prior art systems, and preferably combines the advantages of the stereotactic frame—accuracy, relative low cost, mechanical support—with the advantages of robotic systems—reduced patient morbidity, automatic positioning, intraoperative plan adaptation—and which has a small system size and does not mandate head immobilization.

The disclosures of each of the publications mentioned in this section and in other sections of the specification are hereby incorporated by reference, each in its entirety.

SUMMARY OF THE INVENTION

The present invention seeks to provide a new system for minimally invasive keyhole neurosurgical procedures, based on a miniature robot mounted either on the patient's skull, preferably by means of location pins, or on a head immobilization clamp, or on a fixed stand near the surgical site, such as on the operating table. The robot automatically positions a mechanical guide to support keyhole drilling and insertion of a needle, a probe, or a catheter, based on entry point and target locations predefined by means of a preoperative volume image, such as a CT or MRI scan. The system is based on the same assumptions regarding brain shift and needle bending as stereotactic frames, navigation systems, and available robotic systems.

A novel three-way registration scheme is used in order to establish a common reference frame between the preoperative CT/MRI volume image, the intraoperative patient head location, and the robot location. This registration scheme uses intraoperative surface scanning to provide the link. This is preferably accomplished by acquiring an intraoperative three dimensional surface scan of significant areas of the patient's upper facial features, and which also includes a custom registration jig disposed in a position close to the planned operative site on the patient's head, followed by matching of the intraoperative scanned facial features (without the registration jig) to their respective preoperative geometric models obtained from the CT/MRI volume image. The robot is then mounted in a position known relative to the scanned registration jig, and hence, since the registration jig has been related to the preoperative CT/MRI image by means of the surface scan, in a position which can be related to the preoperative CT/MRI image. Since the surgical sites, such as the entry and target points of the procedure, are known from the preoperative CT/MRI image, the robot pose can thus be related to those entry and target points. The registration jig used is preferably of a novel form, being a wide-angled tetrahedron having different angles between each of its four faces. Because of the comparatively large base angles, the tetrahedron is of low height when viewed from the general direction of the surface scanner, such that all four planes of the tetrahedron can then be seen from a wide range of scanning viewpoints, with a large enough area seen to provide good scan sampling.

Once this registration is performed, the transformation that aligns the planned and actual robot targeting guide location is computed. The robot is then automatically positioned and locked in place so that its targeting guide axis coincides with the entry point/target axis.

Since the facial features of the patient may be subject to movement between the performance of the preoperative CT/MRI scan, when the patient is generally conscious, and the performance of the intraoperative 3-D scan, when the patient may be sedated or anaesthetized, the matching of facial features between these two operations may be subject to inaccuracy. According to a further preferred embodiment of the present invention, the matching between the preoperative CT/MRI image set and the intraoperative scanned image is therefore performed using artificial fiducial markers attached to the head of the patient, such that their position does not move during this registration process.

Prior to acquiring the preoperative MRI/CT, markers, preferably in the form of bone fiducials, are screwed into the dura of the patient's skull under local anesthesia, in a manner similar to that used for the screws of the commonly used stereotactic frame. Then, the CT/MRI image set is acquired, and the surgeon selects the entry and target points according to the preoperative plan. The fiducial markers are also detected in these images, and their location with respect to the entry and target points is known because they are all in the same preoperative image coordinate system.

Intraoperatively, a surface scan is performed in order to determine the intraoperative location of the fiducial markers. However, since the markers are small, and the number of scanned points from them is thus also small, it is difficult to obtain an accurate determination of their position using a 3-D surface scanner. In order to overcome this limitation, a further registration jig, which functions as a fiducial registration jig, is mechanically attached to at least some of the fiducials in a predefined manner, such that its pose relative to the positions of the fiducial markers is known. A surface scan is then obtained as previously, and the well defined features of the fiducial registration jig enable an accurate scan to be obtained. The fiducial registration jig may have any convenient form which is accurately plotted during scanning, such as the tetrahedron described above. The relation between the fiducial registration jig and the fiducial markers is known, and hence also the relation between the intraoperative coordinate system and the preoperative coordinate system and data. Thus the preoperative plan entry and target points can be related to the intraoperative coordinate system, which is that of the robot. In this embodiment, the fiducial registration jig and the fiducial markers replace the face scan of the previous embodiment, the markers behaving like artificial and immovable landmarks on the head of the patient. The advantage of this technique it that it is potentially more accurate since the fiducials do not move from the preoperative to the intraoperative time. The disadvantage is that it requires the additional procedure of insertion of the fiducial markers before acquiring the CT/MRI dataset, which may be uncomfortable for the patient.

The invention of the present application thus seeks to provide an image-guided system for precise automatic targeting of structures inside the brain that is less disadvantageous overall than the prior art systems described hereinabove.

According to a further preferred embodiment of the present invention, the matching of the preoperative images of the patient's skull with those generated intraoperatively is performed in two steps, with a first approximate registration being performed based only on the position of landmarks such as eyes and ears of the patient, while the full accurate registration is performed by large area comparison of surface contours. In such a case, the intraoperative 3D surface scan of the patient's upper facial features preferably includes one or more eyes and face forefront for a frontal scan, or an ear and nose for a lateral acquisition.

Additionally, the system can also optionally be fitted, according to a further preferred embodiment of the present invention, with an integrated video camera system, linked to the preoperative planning module program of the system, and which shows projected on a real time image of the surgical site, a virtual representation of the optimal position for placement of the robot as determined in the preoperative plan, such that the surgeon can duplicate this virtual position on screen with the real robot as he positions the robot base, or a targeting jig to simulate the robot base, at the surgical site. This procedure utilizes an augmented reality display of the patient's head. Alternatively and preferably, the video camera system could be arranged to provide an augmented virtuality display of the patient's head obtained from the preoperative plan data, and including the optimum planned position indicated thereon, and a real-time image of the surgeon's hand holding the robot base or a targeting jig is imposed on this virtual image of the patient's head, thus guiding the surgeon in positioning the robot.

The system hardware consists of: 1) the miniature robot and its controller; 2) a custom robot mounting base, targeting guide, and registration jig; 3) a standard 3D surface scanner; 4) a standard digital video camera and; 5) a PC. The adjustable robot mounting jig attaches the robot base to either the head immobilization frame or to skull-implanted pins or to a stand located close to the operative site. The system software modules preferably include: 1) preoperative planning; 2) intraoperative robot positioning; 3) 3D surface scan processing and 4) three-way registration.

There is thus provided in accordance with a preferred embodiment of the present invention, a system for performing keyhole neurosurgery on a subject, comprising:
(i) an imaging system for generating a three dimensional image set of at least part of the subject's head,
(ii) a preoperative plan utilizing the three dimensional image set, the plan defining at least one neurosurgical procedure on the subject's head,
(iii) a three dimensional surface scanner for generating an intraoperative surface scan of at least part of the subject's head,
(iv) a registration jig for mounting in a position relative to the subject's head such that its pose is defined in the three dimensional scan,
(v) a miniature robot for mounting in a predetermined position relative to the registration jig, and
(vi) a registration procedure utilizing the surface scan to define the robot position relative to the three dimensional image set, such that the robot may intraoperatively perform the at least one neurosurgical procedure defined by the preoperative plan.

The system may also preferably comprise a targeting guide supported by the robot to direct a surgical tool, and wherein the neurosurgical procedure delineates at least one entry point on the subject's head and at least one target point within the subject's head, and wherein the robot is adjusted to align the targeting guide to direct the surgical tool from the entry point towards the target point.

In either of the above two embodiments, the registration procedure preferably matches the surface scan of at least part of the subject's head with a surface model of corresponding parts of the subject's head obtained from the three dimensional image set.

In accordance with another preferred embodiment of the present invention, any of the above-mentioned systems may also comprise a plurality of fiducial markers mounted on the head of the subject, and wherein the surface scan of at least part of the subject's head includes the location of the fiducial markers, and the registration procedure matches the location of the fiducial markers with the locations of the fiducial markers obtained from the three dimensional image set. At least one of these fiducial markers may preferably be a bone screw attached to the subject's head. Furthermore, such a system comprising fiducial markers may also preferably include a fiducial registration jig for attaching in a predefined manner to at least some of the fiducial markers, and wherein the surface scan of at least part of the subject's head includes a scan of the fiducial registration jig, such that the location of the fiducial markers is determined from the location of the fiducial registration jig.

In accordance with a further preferred embodiment of the present invention, the above-mentioned surface scan of at least part of the subject's head may preferably comprise a plurality of landmark features of the subject's head, and the registration procedure then matches the landmark features to corresponding landmark features obtained from the three dimensional image set. The plurality of landmark features of the subject's head preferably comprises at least one anatomical feature of the subject. Alternatively and preferably, the plurality of landmark features of the subject's head may comprise at least one fiducial marker mounted on the head of the subject, in which case at least one of the at least one fiducial markers may be a bone screw attached to the subject's head. When such fiducial markers are so incorporated, the system also may preferably include a fiducial registration jig for attaching in a predefined manner to at least one of the fiducial markers, and the surface scan of at least part of the subject's head then also includes a scan of the fiducial registration jig, such that the location of the at least one fiducial marker is determined from the location of the fiducial registration jig.

In the above-mentioned systems in which the surface scan includes landmark features, it may also preferably comprise a significant area of facial contours of the subject's head, and the registration procedure then also matches contours of the significant area of facial contours of the subject's head to contours of the corresponding area obtained from the three dimensional image set.

Furthermore, in accordance with yet another preferred embodiment of the present invention, in any of the above described systems, the three dimensional image set is preferably obtained preoperatively by at least one of CT and MRI. Additionally, either or both of the registration jig and the miniature robot may be mounted on the subject's head, or on a head immobilization clamp, or are mounted on a fixed stand disposed near the subject's head.

There is also provided in accordance with a further preferred embodiment of the present invention, any of the above-described systems, wherein the three dimensional surface scanner is any one of an optical laser scanner, a plurality of video cameras, a structured light source with a single video camera, and a radar scanner. Furthermore, the registration jig may preferably comprise a tetrahedron having any pair of its four faces mutually aligned at different angles.

In accordance with yet another preferred embodiment of the present invention, there is also provided any of the above-described systems and also comprising a video camera disposed in a predetermined position relative to the three dimensional surface scanner and displaying a real-time image of the subject's head, and in which information is provided to the video camera from the preoperative plan to show on the real-time image a virtual indication of an approximate position for placement of the miniature robot. Such a system then preferably also comprises a positioning jig used to indicate the position of the robot during approximate placement, and the virtual indication is then a virtual representation of the positioning jig.

Finally, in all of the above-described systems, the system is operative without the need for an external navigation system.

There is further provided in accordance with yet another preferred embodiment of the present invention, a three dimensional registration jig comprising a tetrahedron having any pair of its four faces mutually aligned at different angles. Such a three dimensional registration jig preferably provides unambiguous data regarding its pose when scanned by a three dimensional scanner. According to a further preferred embodiment of the present invention, the tetrahedron preferably has a sufficiently small height in the general scanning direction of the scanner that all four planes can be seen from a wide range of scanning angles.

There is also provided in accordance with a further preferred embodiment of the present invention, a method of performing keyhole neurosurgery on a subject, comprising the steps of:
(i) generating a three dimensional image set of at least part of the subject's head,
(ii) utilizing the three dimensional image set to produce a preoperative plan, the plan defining at least one neurosurgical procedure on the subject's head,
(iii) providing a three dimensional surface scanner disposed such that it can generate an intraoperative surface scan of at least part of the subject's head,
(iv) mounting a registration jig in a position relative to the subject's head such that its pose is defined in the intraoperative surface scan,
(v) scanning at least part of the subject's head to generate a three dimensional intraoperative surface scan of the subject's head with the registration jig,
(vi) mounting a miniature robot in a predetermined position relative to the registration jig, and
(vii) performing a registration procedure utilizing the surface scan to define the robot position relative to the three dimensional image set, such that the robot may intraoperatively perform the at least one neurosurgical procedure defined by the preoperative plan.

The method may also preferably comprise the step of providing a targeting guide supported by the robot to direct a surgical tool, and in which the neurosurgical procedure delineates at least one entry point on the subject's head and at least one target point within the subject's head, the method also comprising the further step of adjusting the robot to align the targeting guide to direct the surgical tool from the entry point towards the target point.

In either of the above two embodiments, the registration procedure preferably matches the surface scan of at least part of the subject's head with a surface model of corresponding parts of the subject's head obtained from the three dimensional image set.

In accordance with another preferred embodiment of the present invention, any of the above-mentioned methods may also comprise the step of mounting on the head of the subject a plurality of fiducial markers, and the step of scanning at least part of the subject's head then includes scanning the locations of the fiducial markers, and the registration procedure then matches the locations of the fiducial markers with the locations of the fiducial markers obtained from the three dimensional image set. In this method, at least one of these fiducial markers may preferably be a bone screw attached to the subject's head. Furthermore, such a method comprising fiducial markers may also preferably include the steps of providing a fiducial registration jig and attaching it in a predefined manner to at least some of the fiducial markers, and wherein the surface scan of at least part of the subject's head includes a scan of the fiducial registration jig, such that the location of the fiducial markers is determined from the location of the fiducial registration jig.

In accordance with a further preferred embodiment of the present invention, the above-mentioned surface scan of at least part of the subject's head may preferably comprise a plurality of landmark features of the subject's head, and the registration procedure then matches the landmark features to corresponding landmark features obtained from the three dimensional image set. In this method, the plurality of landmark features of the subject's head preferably comprises at least one anatomical feature of the subject. Alternatively and preferably, the plurality of landmark features of the subject's head may comprise at least one fiducial marker mounted on the head of the subject, in which case at least one of the at least one fiducial markers may be a bone screw attached to the subject's head. When the method makes use of such fiducial markers, it may also preferably include the step of providing a fiducial registration jig for attaching in a predefined manner to at least one of the fiducial markers, and the surface scan of at least part of the subject's head then also includes a scan of the fiducial registration jig, such that the location of the at least one fiducial marker is determined from the location of the fiducial registration jig.

In the above-mentioned methods in which the surface scan includes landmark features, it may also preferably comprise a significant area of facial contours of the subject's head, and the registration procedure then also preferably matches contours of the significant area of facial contours of the subject's head to contours of the corresponding area obtained from the three dimensional image set.

Furthermore, in accordance with yet another preferred embodiment of the present invention, in any of the above described methods, the three dimensional image set is preferably obtained preoperatively by at least one of CT and MRI. Additionally, either or both of the registration jig and the miniature robot may be mounted on the subject's head, or on a head immobilization clamp, or are mounted on a fixed stand disposed near the subject's head.

There is also provided in accordance with a further preferred embodiment of the present invention, any of the above-described methods, wherein the three dimensional surface scanner is any one of an optical laser scanner, a plurality of video cameras, a structured light source with a single video camera, and a radar scanner. Furthermore, the registration jig may preferably comprise a tetrahedron having any pair of its four faces mutually aligned at different angles.

In accordance with yet another preferred embodiment of the present invention, there is also provided any of the above-described methods and also comprising the step of disposing a video camera in a predetermined position relative to the three dimensional surface scanner and displaying a real-time image of the subject's head, and in which information is provided to the video camera from the preoperative plan to show on the real-time image a virtual indication of an approximate position for placement of the miniature robot. Such a method then preferably also comprises the step of providing a positioning jig to indicate the position of the robot during approximate placement, and the virtual indication is then a virtual representation of the positioning jig.

Finally, in all of the above-described methods, there is no need for external navigation.

BRIEF DESCRIPTION OF THE DRAWINGS

The present invention will be understood and appreciated more fully from the following detailed description, taken in conjunction with the drawings in which:

FIGS. 1A to 1C illustrate schematically a skull-mounted miniature robot of an image-guided robotic keyhole neurosurgery system according to a preferred embodiment of the present invention; FIG. 1A shows the robot mounted on a model of a skull, FIG. 1B shows the base mounting pins, and FIG. 1C shows the robot mounting base on the skull;

FIGS. 3A and 3B illustrate aspects of the preoperative planning module program of the system of the present invention; FIG. 3A shows schematically the choice of the entry and target points in an image of the patient's head, generated by the preoperative planning module, and FIG. 3B shows the range of robot placements offered to the surgeon by the preoperative planning module;

DETAILED DESCRIPTION OF PREFERRED EMBODIMENTS

Figure 1A:
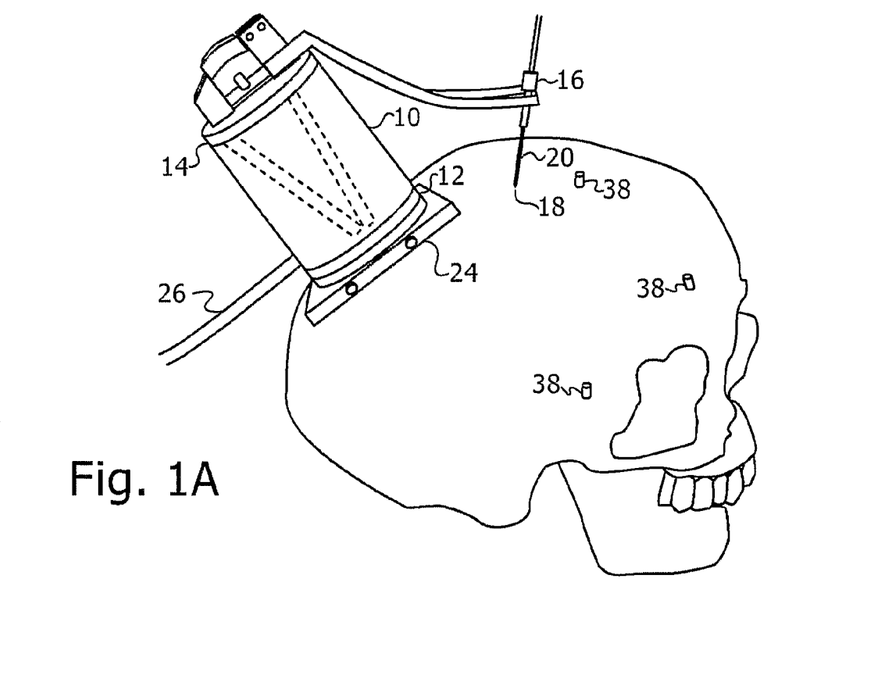

Reference is now made to FIG. 1A, which illustrates schematically a miniature robot 10 in use in an image-guided robotic keyhole neurosurgery system according to a preferred embodiment of the present invention. The miniature robot 10 preferably has a parallel structure with six degrees of freedom, though robots with less degrees of freedom can also be used, and it is preferably directly mounted on the patient bony structure or on a fixed stand near the surgical site.

In FIGS. 1A to 1D and in some of the other drawings of this application, the robot is shown mounted on a model skull, as used in experimental studies of the system, though it is to be understood that in the real life situation, the head of the patient takes the place of the skull. A preferred type of miniature robot for use in the system of the present invention has been described in U.S. Pat. No. 6,837,892 for "Miniature bone-mounted surgical robot" to M. Shoham, and is supplied by Mazor Surgical Technologies Ltd., of Caesarea, Israel. This robot consists of a fixed platform 12 that attaches to a mounting plate 24 attached either to the patient's skull or to a fixed stand, and a moving platform 14 connected in parallel by six independent linear actuators. The moving platform is fitted with a custom targeting guide 16. The preferred type of robot shown in FIG. 1A has dimensions of 5×8×8 cm, its weight is 250 grams, its work volume about 15 cm$^3$, and its positional accuracy is 0.1 mm, which is very adequate for neurological clinical applications, and better that that of stereotactic frames and commercial tracking systems.

The robot is preferably designed to operate in a semi-active mode: it positions and orients the targeting guide 16 to a predefined location, and locks itself there, becoming a rigid structure. It can withstand lateral forces of 10N. The robot may be placed in a fully sterilizable cover and may be operated via a single cable 26 from a controller preferably housed in a separate unit.

Such a robot may be viewed as a precise, fine positioning device, as described in the article by M. Shoham, et al., "Bone-mounted miniature robot for surgical procedures: concept and clinical applications", IEEE Trans. on Robotics and Automation, Vol. 19 (5), 2003, pp 893-901. Its advantages stem from its small size and design: 1) it can be mounted directly on the patient bone, and thus does not require tracking or head immobilization; 2) it is intrinsically safe, as its power and motion range are restricted; 3) it is unobtrusive; 4) it is covered by a sterilizable sleeve; and 5) it is of considerably lower cost than larger prior art robots. It has a disadvantage that its work volume and range of motion is small, such that this limitation has to be compensated for by using a preliminary coarse positioning method.

Such a robot has been described in the prior art for various orthopedic procedures, such as in the above mentioned U.S. Pat. No. 6,837,892, in PCT Application published as WO 2003/105,659 and in PCT Application published as WO2004/100758. Its use in the present invention for keyhole neurosurgeries has a number of common features with the prior art, such as 1) precise targeting with mechanical guidance; 2) small work volume of the surgery, and 3) the need for preoperative image planning, and a number of differences with the prior art uses, such as 1) software for preoperative planning; 2) three-way registration basis and procedure; 3) robot fixation and targeting guides; and 4) the need for placing the robot in the vicinity of the entry point (coarse positioning).

The surgical protocol of the system includes the following steps. A preoperative volume CT/MRI image or image set of the patient is acquired, without the need for any markers or a frame. Next, with the preoperative planning module, the surgeon defines on the image set the desired entry point 18 or points and the desired target location or locations, and determines the robot mounting type (head clamp or skull, depending on clinical criteria) and the desired robot location.

Figure 1B:
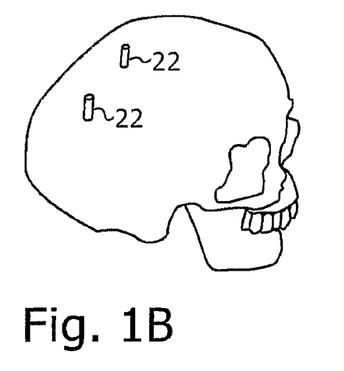
Figure 1C:
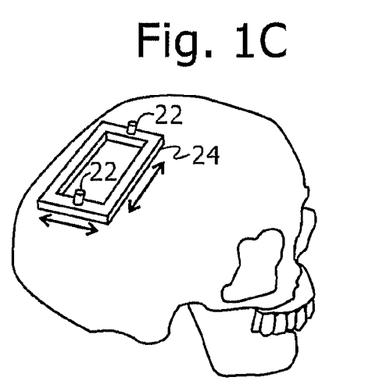

Intraoperatively, under general or local anesthesia and following sterile draping of the scalp, the surgeon places the robot approximately in its planned location, guided by a video-based intraoperative module. This procedure is necessary because of the comparatively limited operating range of the miniature robot relative to the skull dimensions. When mounted on the skull, two 4 mm pins 22 are preferably screwed under local anesthesia into the skull and the robot mounting base 24 is attached to them. This is illustrated in FIGS. 1B and 1C. The robot mounting base 24 preferably has some linear adjustment in two dimensions, as indicated by the arrows in FIG. 1C.

Figure 1D:
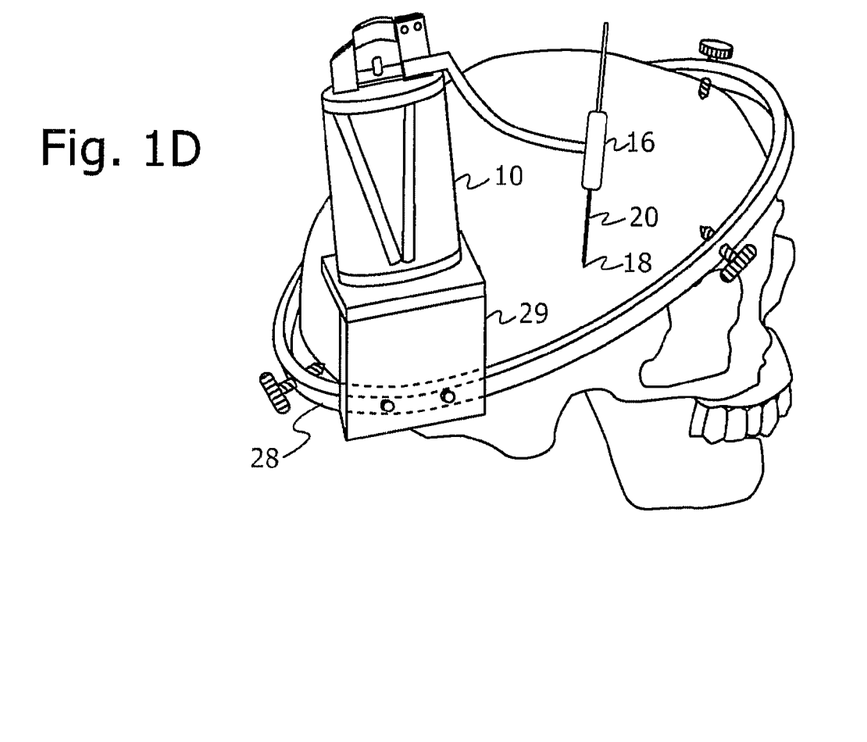
FIG. 1D illustrates schematically the miniature robot of FIG. 1A mounted on a head clamp.

When the robot is mounted on a head frame such as a Mayfield clamp 28, as shown in FIG. 1D, the robot 10 is preferably attached thereto by means of an adjustable mechanical arm or mounting plate 29. Alternatively and preferably, the robot can be mounted in a similar manner directly on the operating table close to the patient's head, with the head immobilized by a head clamp.

In the following description, a preferred embodiment is used in which the robot is mounted on a base which is mounted directly on the skull of the patient, as shown in FIGS. 1B and 1C, but it is to be understood that the system is equally operable with the robot mounted on a head clamp or on a stand close to the patient's skull, with the relevant amendments to the procedure or apparatus as required.

Figure 2:
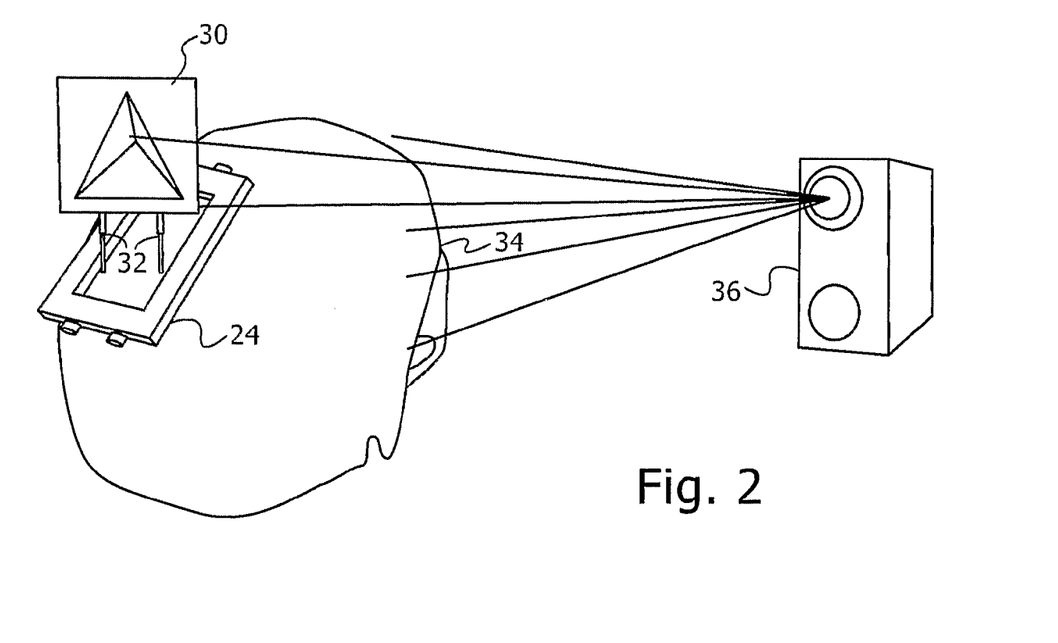
FIG. 2 illustrates schematically the location of the special registration jig of the present invention on the robot mounting base of FIG. 1C, with the three dimensional surface scanner generating a surface scan of the skull.

Next, and with reference to FIG. 2, a special registration jig 30 is placed in a predetermined position, which has a known relation to the position of the robot, whether mounted directly on the patient's skull, or on a head clamp, or on a fixed stand near the patient's head. This predetermined position can preferably be achieved by providing the registration jig with feet 32 for insertion into defined sockets in the mounting base 24. The system of the present invention also includes a three dimensional surface scanner 36, positioned facing the patient and the robot, so that a 3-D surface scan including both the patient forehead 34 or ear (frontal or lateral scan, depending on robot location) and the registration jig 30 can then be acquired. The 3-D surface scanner 36 is preferably a laser scanner, or any other three dimensional surface scanning device that provides accurate 3D surface data in the form of points or surface patches, such as an optical scanner, two or more video cameras, a structured light source with one video camera, or a millimetric wave radar system. According to a further preferred embodiment of the present invention, the 3-D surface scanner is used to provide an intraoperative scan of the position of fiducial markers, inserted before the preoperative CT/MRI imaging, as explained in the Summary Section hereinabove. Such optional fiducial markers 38 for use in this embodiment are shown in FIG. 1A mounted in the head of the patient. In the representation of FIG. 2, an additional fiducial registration jig would be preferably attached to some of the fiducial markers during scanning, to enhance the scanning accuracy.

The registration jig 30 is then replaced by the robot 10 with the targeting guide on it, and since the robot sits on the mounting base in a known position relative to the position of the registration jig, the intraoperative 3-D scan is therefore also effectively correlated to the robot position. The registration module automatically computes the offset between the actual targeting guide orientation, as determined by this intraoperative registration, and the desired targeting guide orientation, as determined by the preoperative plan. It then positions and locks the robot so that the targeting guide axis coincides with the planned needle insertion trajectory. The surgeon can then manually insert the needle 20, probe or catheter to the desired depth. Alternatively and preferably, the miniature robot can be programmed to make small translational adjustments, typically up to ±10 mm, of the needle along the insertion axis. On surgeon demand, the system automatically repositions the robot for each of the predefined trajectories. The intraoperative plan can be adjusted during the surgery by deleting and adding new target points. The system is programmed to automatically compute the trajectories and the corresponding robot positions.

Figure 3A:
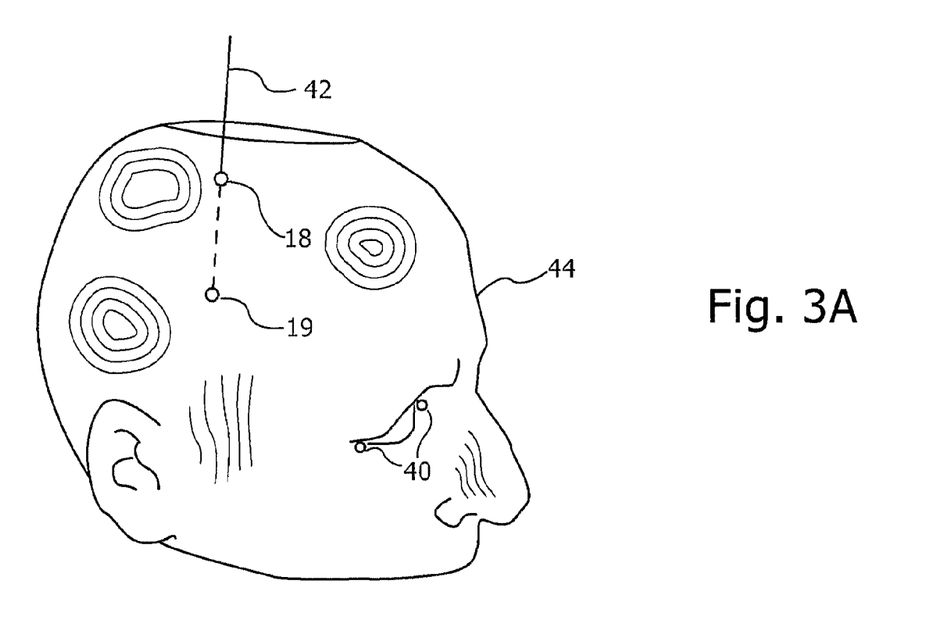

FIGS. 1A to 1D and FIG. 2 describe the functional operation of the system of the present application according to a first preferred embodiment. According to further preferred embodiments of the present invention, a number of computational modules, with associated hardware are used in order to facilitate the accurate operation of the system. Referring now to FIG. 3A, the system includes a preoperative planning module which inputs the CT/MRI image set and geometric models of the robot, its work volume and the targeting guide. It then automatically builds from the CT/MRI image, a 3-dimensional model of the skull and forehead/ear surfaces 44. This 3-D surface model will be used later for matching with a 3-D surface scan generated intraoperatively by a 3-D optical scanner, to enable registration of the preoperative data with the true life intraoperative patient situation, as is known in the art. FIG. 3A is a part of one of the screens of this preoperative planning module, showing the 3-dimensional model of the head built from the CT/MRI data.

The preoperative planning module extracts a number of landmarks 40 (eyes or ear) to be used later for coarse registration. These landmarks are used because of the otherwise generally featureless nature of the skull. Such coarse registration is used in order to make an initial approximate estimation of the desired position of the robot. Accurate registration, on which the accuracy of the entire system is based, is achieved from this initial approximate registration, by the use of surface comparison algorithms as will be explained hereinbelow. The module allows interactive visualization of the CT/MRI slices (axial, cranial and neurosurgical views) and the 3D skull surface, and enables the surgeon to define entry points 18 and target points 19, visualize the resulting needle trajectories 42, as shown in FIG. 3A, and to make spatial distance measurements.

According to one preferred procedure, the skull and forehead/ear surface models are constructed in two steps. First, the CT/MRI images are segmented with a low-intensity threshold to separate the skull pixels from the air pixels. The ear tunnel pixels are then identified and filled. The surfaces are then reconstructed, preferably with the enhanced Marching Cubes surface reconstruction algorithm. The eye/ear landmarks are computed preferably by identifying the areas of maximum curvature with Taubin's curvature estimation method on triangular meshes as described in the article by G. Taubin, "Estimating the tensor of curvature of a surface from a polyhedral approximations", ICCV, pp. 902-907, 1995.

Figure 3B:
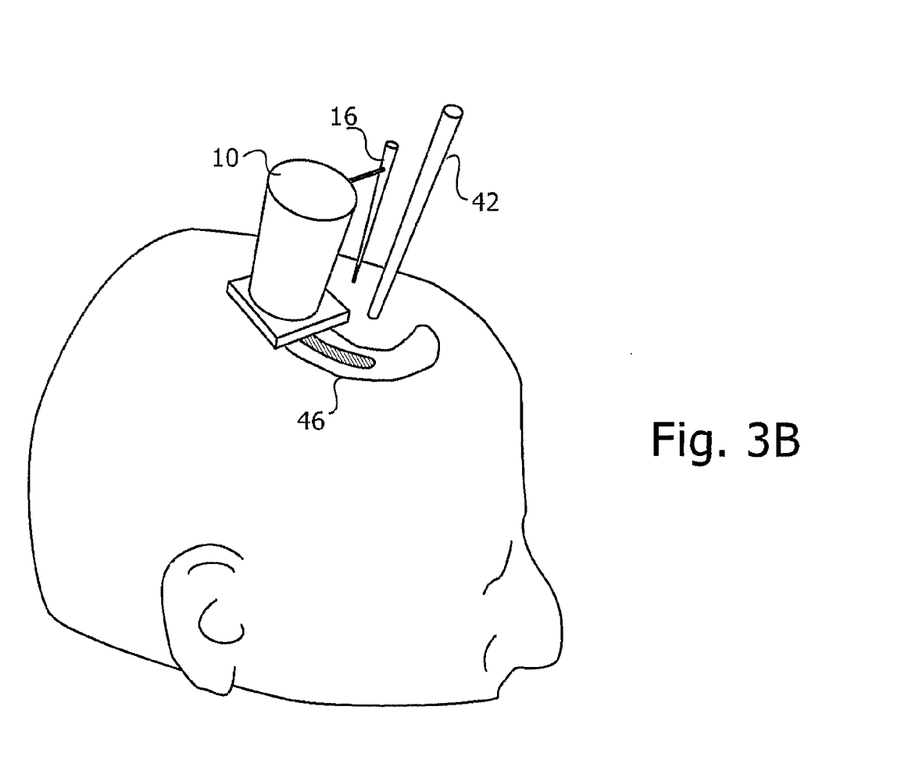

Based on the surgeon-defined entry 18 and target 19 points, and the robot mounting mode (skull or head clamp), the module automatically computes the optimal placement of the robot base and its range. This step is necessary because of the limited work volume of the miniature robot relative to the skull dimensions. The optimal robot base placement is such that the planned needle trajectory 42 is at the center of the robot work volume. Placements away from the optimal placement are assigned a score based on how far they are from the robot work volume center. The results are graphically shown to the surgeon, as shown in FIG. 3B by the shaded regions 46 of the skull representation. The score level of the various regions of the optimal placement area can be shown by different colors within the area. The surgeon can then select an optimal position that also satisfies clinical criteria, such as avoiding the cranial sinuses, temporal muscle, or the emissary vein. The output of the preoperative planning module thus includes the surgical plan (entry and target points), the planned robot base placement, and the face surface mesh and landmarks.

Figure 4:
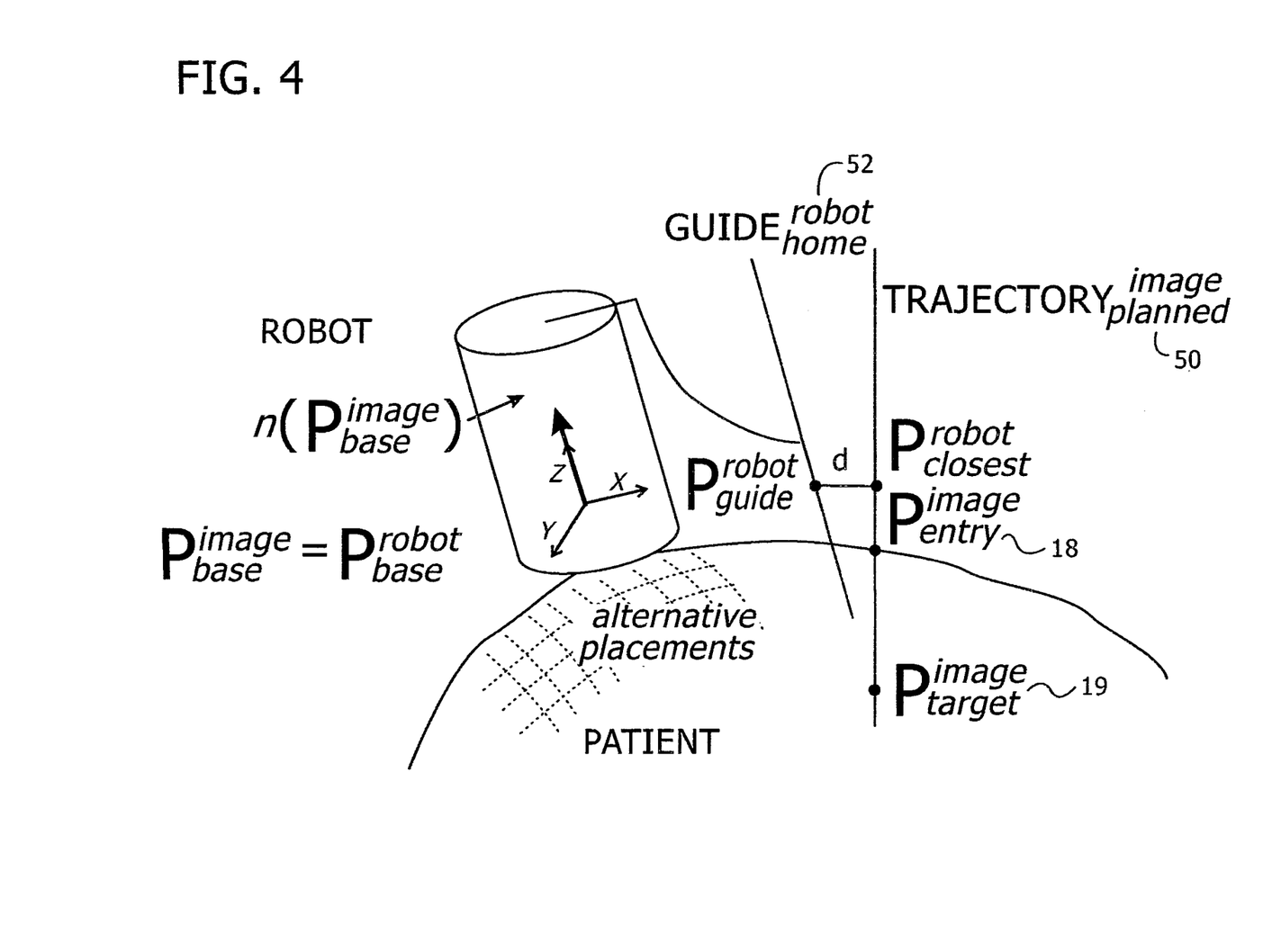
FIG. 4 illustrates schematically the computation method for the preoperative robot placement, which results in the displayed images shown in FIGS. 3A and 3B.

Reference is now made to FIG. 4 which illustrates schematically the computation method for preoperative robot placement. The goal is to compute the transformation that aligns the planned trajectory $^{image}_{planned}$ 50, (defined by the entry point $P^{image}_{entry}$ 18 and target point $P^{image}_{target}$ 19) in image coordinates, to the targeting guide axis with the robot in its home position, guide$^{home}_{robot}$ 52, in robot coordinates.

Figure 5:
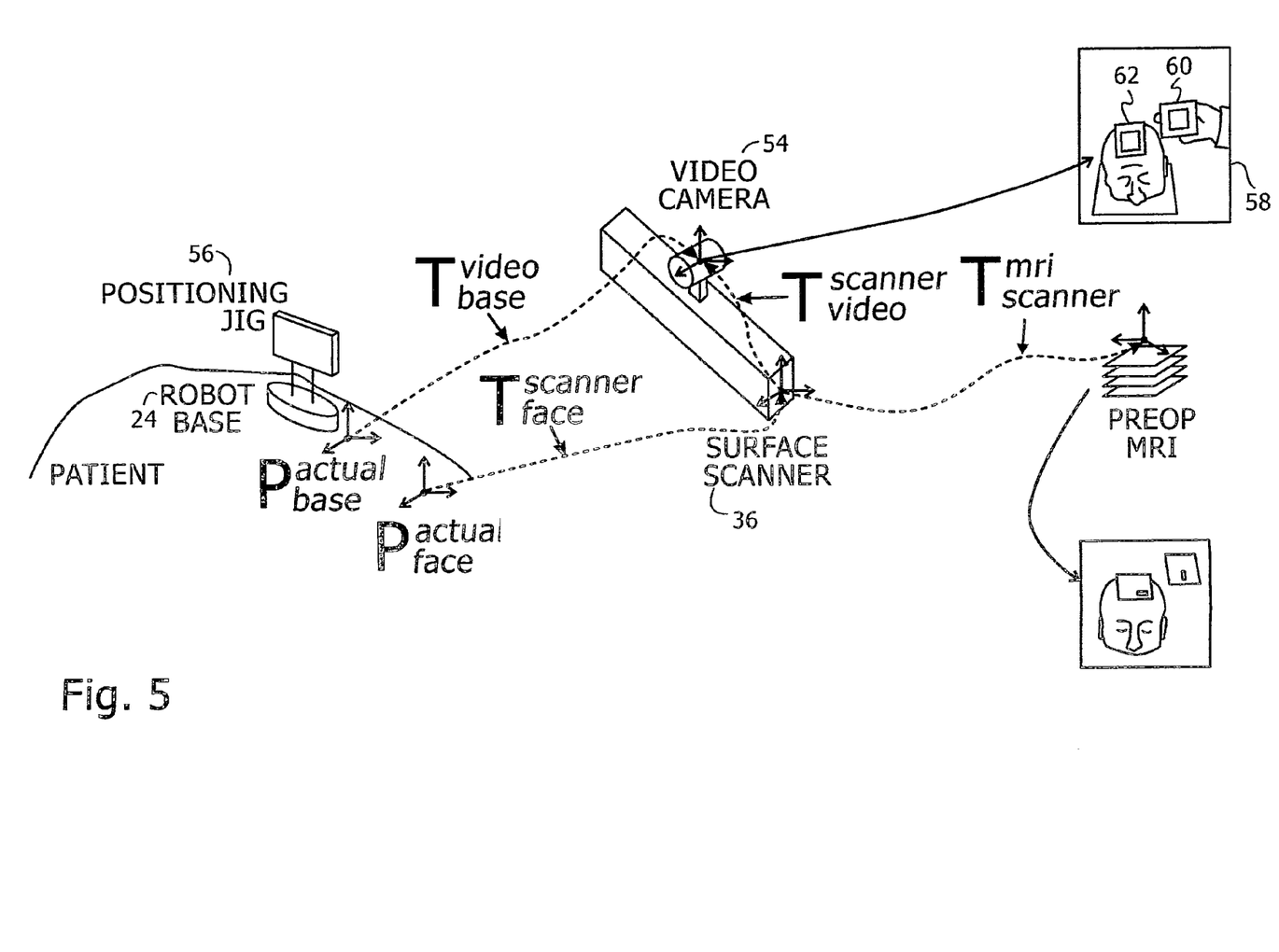
FIG. 5 is a schematic view of the system of the present invention, illustrating the use of an integrated video camera to assist the surgeon in adjusting the position and orientation of the robot mounting base in its optimum position.

Reference is now made to FIG. 5, which illustrates how the intraoperative robot positioning module is operative in assisting the surgeon to place the robot base 24 close (within 5 mm) to its planned position, both for skull and frame-mounted cases. Given the small robot work volume and the lack of anatomical landmarks on the skull, this coarse positioning is necessary to avoid deviations of more than the robot work envelope from the planned position. These deviations can severely restrict or even invalidate the preoperative plan.

FIG. 5 is a schematic view of the system of the present invention, illustrating the use of an integrated video camera 54 to assist the surgeon in adjusting the position and orientation of the robot mounting base in its optimum position. Use is made of a dedicated positioning jig 56 inserted into the mounting base 54, and the position of the positioning jig is adjusted until it matches the planned location determined by the intraoperative robot positioning computation. The object of this operation is to superimpose the planned robot base position onto the real time video camera image 58 at its desired planned position. The video monitor preferably shows real-time, augmented reality images 58 consisting of a video image of the actual patient skull and the positioning jig with mounting base in the hand of the surgeon 60, and, superimposed on it, a virtual image of the same jig indicating the robot base in its desired preplanned location 62. The surgeon can then adjust the position and orientation of the positioning jig until it matches the planned location, and this then defines the optimum mounting base position. FIG. 5 also shows at the bottom right hand corner, an alternative display screen of the video camera system showing an augmented virtuality display of the patient's head, using the preferred method mentioned and described in the Summary of the Invention Section of this application.

The video camera is mounted either directly on the 3-D surface scanner 36 (used for comparing the CT/MRI image generated face surface model with the intraoperative surface scan of the patient's features), or at a known location relative to the scanner, and is pre-calibrated, so that the transformation between the two coordinate systems, $T^{video}_{scanner}$ is known in advance. A 3-D surface scan of the face is acquired and matched to the geometric face model with the same method used for the three-way registration described below. This establishes the transformation between the preoperative plan and the scanner, $T^{scanner}_{plan}$. By composing the two transformations, the transformation between the preoperative plan and the video, $T^{video}_{plan}$ can be obtained.

According to a further preferred embodiment of the present invention, the system also includes a surface scan processing module, which automatically extracts three sets of points from the intraoperative 3D surface scan generated by the 3-D surface scanner 36: 1) a forehead (frontal scan) or ear cloud of points (lateral scan); 2) preferably four eye or ear landmark points; and 3) the registration jig cloud of points (when the jig is present in the scan). The forehead/ear cloud of points is computed by first isolating the corresponding areas and removing outliers. The landmark points are extracted by fitting a triangular mesh and identifying the areas of maximum curvature as in the CT/MRI images. The jig cloud of points is computed by isolating the remaining points.

Figure 6:
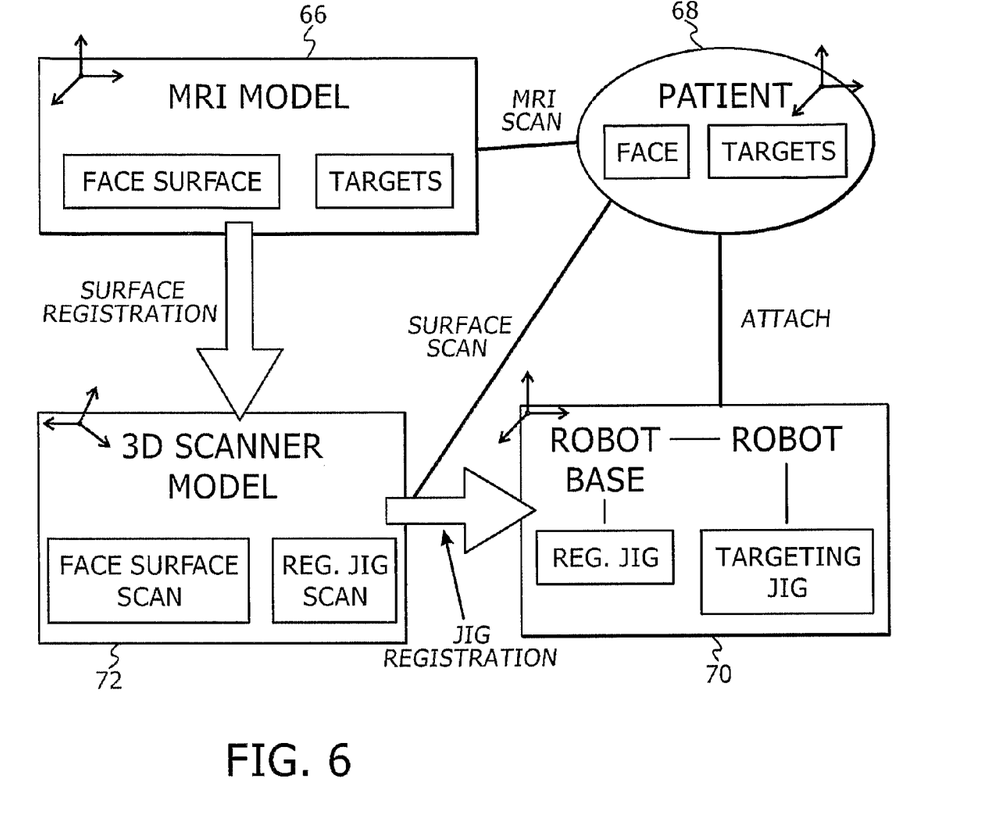
FIG. 6 illustrates schematically the associative links in the novel three-way registration procedure, according to a further preferred embodiment of the present invention.

Reference is now made to FIG. 6, which illustrates schematically the associative links in the novel three-way registration procedure, according to a further preferred embodiment of the present invention. The three-way registration module computes the transformation $T^{robot}_{pan}$ that establish a common reference frame between the preoperative CT/MRI data 66, the intraoperative locations of the robot mounting base 68 and the patient head 70. The connecting link between these three independent sets of coordinates is established by means of the 3-D laser surface scan 72 of features of the patient's head.

Two transformations are computed to this end: $T^{scanner}_{plan}$, the preoperative plan to intraoperative patient face/ear scan data transformation, and $T^{scanner}_{robot}$, the robot mounting base to scanner transformation.

The transformation $T^{scanner}_{plan}$ is preferably computed by first computing a coarse correspondence between the four pairs of preoperative/intraoperative landmark points, such as by using Horn's closed form solution. The transformation is then refined to the highest accuracy possible, such as by use of the robust Iterative Closest Point (ICP) registration, as described by Besl, P. J. et al., in "A method for registration of 3D shapes", IEEE Trans. on Pattern Analysis and Machine Intelligence, Vol. 14(2), 1992, and preferably performed between a small subset of the surface scan points and the CT/MRI points on the face/ear surface. This provides a highly accurate intraoperative surface scan match with the surface model generated from the preoperative CT/MRI data.

Figure 7:
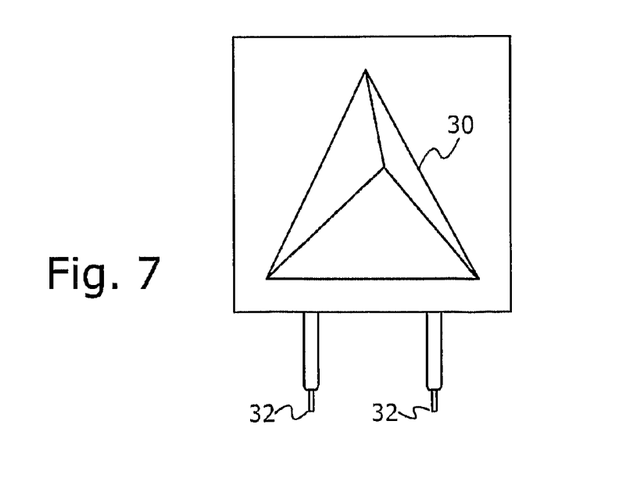
FIG. 7 illustrates schematically one preferred embodiment of the registration jig shown in FIG. 2, in the form of a wide-angled tetrahedron.

The transformation $T^{scanner}_{robot}$ is obtained from the custom design of the registration jig, as shown schematically in FIG. 7. According to one preferred embodiment, the registration jig 30 is a wide-angled tetrahedron that is attached to the robot mounting base, preferably by means of locating feet 32. It is designed so that all four planes can be seen from a wide range of scanning viewpoints, with sufficient area for adequate scan sampling. To facilitate plane identification, the angles between all adjacent tetrahedron faces are different.

The registration jig model may preferably be matched to the surface scanner data by any of the methods known in the art. The scanner identifies the three visible planes of the tetrahedron, and determines the four intersection points of these three planes. These intersection points can then be correlated to the known model intersection points. One preferred method of performing this matching is by first computing a Delaunay triangulation of the registration jig cloud of points. Next, the normals of each mesh triangle vertex are computed and classified into five groups according to their value: four groups correspond to each one of the planes of the registration jig, and one to noise. A plane is then fitted to the points in each of the groups. The four points corresponding to the intersection between any three planes are the registration jig vertices. The affine transformation between these four points and the corresponding ones in the model is then computed. Finally, an ICP rigid registration on the plane points is computed to further reduce the error. The actual robot mounting base location with respect to the preoperative plan is determined from this transformation, and the targeting guide location is then determined from the robot mounting base location and the robot characteristics.

The systems of the above-described embodiments of the present invention, thus allow for automatic precise targeting in minimally invasive keyhole neurosurgery that largely overcomes many of the limitations of existing solutions. The systems eliminate the morbidity and head immobilization requirements associated with stereotactic frames, eliminate the line-of-sight and tracking requirements of navigation systems, and provide steady and rigid mechanical guidance without the bulk and cost of large robots. In terms of the characteristics described in table 1 above, it is believed that systems constructed according to the present invention are capable of achieving +++ ratings for all of the characteristics, except that for accuracy, range and cost, only a ++ rating would be achieved. Furthermore, head fixation is not mandatory in most embodiments. Such a combination of characteristics is not believed to be currently achieved by the prior art methods shown.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system for performing neurosurgery on a subject's head, comprising:
    a control system adapted to use a preoperative plan for performing at least one neurosurgical procedure on the subject's head, said preoperative plan being derived from a preoperatively generated three dimensional image set of at least part of the subject's head;
    a three dimensional scanner for generating an intraoperative surface scan of anatomical features of at least part of the subject's head;
    fixation elements configured for mounting in a fixed position on the subject's head;
    a registration jig comprising a tetrahedron having different angles different angles between each pair of its four faces for mounting on said fixation elements, a position and orientation of said registration jig being defined in said intraoperative three dimensional scan by three dimensional imaging of the tetrahedron faces; and
    a miniature robot adapted for mounting on said fixation elements in a predetermined position relative to that of said registration jig, wherein a position of said miniature robot is fixed relative to said subject's head;
    said control system configured to match at least some anatomical features in said intraoperative surface scan of at least part of the subject's head with corresponding anatomical features in a model of corresponding parts of the subject's head obtained from said preoperatively generated three dimensional image set, such that the position of said miniature robot, when mounted on said fixation elements, is also defined relative to said preoperatively generated three dimensional image set in order to control the position of said miniature robot according to said at least one neurological procedure, wherein said control system is further configured to control said miniature robot to intraoperatively perform said at least one neurosurgical procedure defined by said preoperative plan.

2. A system according to claim 1 wherein said position of said miniature robot is defined relative to said subject's head by first defining the position of said registration jig using said scanner, and said miniature robot is mounted on said fixation elements in a predetermined position relative to the position of said registration jig.

3. A system according to claim 1 wherein said position of said miniature robot is defined relative to said subject's head by determining the position of said fixation elements, and mounting said miniature robot with its base directly on said fixation elements.

4. A system according to claim 1 wherein said position of said miniature robot is defined relative to said subject's head by defining the position of said registration jig when mounted on said robot, using said scanner.

5. A system according to claim 1 further comprising a targeting guide supported by said miniature robot to direct a surgical tool, wherein said at least one neurosurgical procedure delineates at least one entry point on the subject's head and at least one target point within the subject's head, and wherein said miniature robot is adjusted to align said targeting guide to direct said surgical tool from said entry point towards said target point.

6. A system according to claim 1 further comprising a plurality of fiducial markers configured to be mounted on the subject's head, wherein said surface scan of at least part of the subject's head includes locations of said fiducial markers, and said control system matches said locations of said fiducial markers with locations of said fiducial markers obtained from said preoperatively generated three dimensional image set.

7. A system according to claim 6, and wherein said miniature robot is mounted in a fixed position relative to said fiducial markers.

8. A system according to claim 6, further including a fiducial registration jig for attaching in a predefined manner to at least some of said fiducial markers, and wherein said surface scan of at least part of the subject's head includes a scan of said fiducial registration jig, wherein said location of said fiducial markers is determined from a location of said fiducial registration jig.

9. A system according to claim 6 and wherein at least one of said fiducial markers is a bone screw configured to be attached to the subject's head.

10. A system according to claim 1 wherein said surface scan of at least part of the subject's head comprises a plurality of landmark features of said subject's head, and said control system matches said landmark features to corresponding landmark features obtained from said preoperatively generated three dimensional image set.

11. A system according to claim 1 and wherein at least one of said registration jig and said miniature robot is mounted on either of a head immobilization clamp or a fixed stand adapted to be disposed near the subject's head.

12. A system according to claim 1, wherein said miniature robot has a working volume and range which are small relative to the skull of said subject, said system further comprising a video camera disposed in a predetermined position relative to said three dimensional scanner, and displaying a real-time image of the subject's head, wherein information is provided to said video camera from said preoperative plan to show on said real-time image a virtual indication of an approximate position for placement of said miniature robot.

13. A system according to claim 12 wherein said miniature robot has a working volume of the order of 15 cm$^3$.

14. A system according to claim 1, wherein said three dimensional scanner is an optical scanner such that said intraoperative surface scan of anatomical features of at least part of the subject's head is an optical surface scan.

15. A system according to claim 1, wherein said tetrahedron has base angles sufficiently large such that all four planes of said tetrahedron can be seen from a wide range of scanning viewpoints.

16. A method of performing neurosurgery on a subject's head, comprising the steps of:
generating a preoperative three dimensional image set of at least part of the subject's head;
utilizing said preoperative three dimensional image set to define a preoperative plan for performing at least one neurosurgical procedure on the subject's head;
mounting fixation elements in fixed positions on the subject's head following generation of said preoperative three dimensional image set of at least part of the subject's head;
mounting a registration jig comprising a tetrahedron having different angles between each pair of its four faces on the fixation elements, wherein a position and orientation of said registration jig is defined in said intraoperative scan by three dimensional imaging of the tetrahedron faces;
providing a three dimensional scanner and scanning at least part of the subject's head to generate a three dimensional intraoperative surface scan of the subject's head including said registration jig;
mounting a miniature robot on said fixation elements wherein the position of the miniature robot is fixed relative to the subject's head,
performing a registration procedure by matching at least some anatomical features in said intraoperative surface scan of at least part of the subject's head with corresponding anatomical features in a model of corresponding parts of the subject's head obtained from said preoperatively generated three dimensional image set, and utilizing said registration procedure to define said robot position relative to said preoperative three dimensional image set in order to control a position of said miniature robot according to said at least one neurosurgical procedure, and
controlling said miniature robot to intraoperatively perform said at least one neurosurgical procedure defined by said preoperative plan.

17. A method according to claim 16 wherein the position of said miniature robot is defined relative to said subject's head by first defining the position of said registration jig relative to said subject's head using said scanner, and mounting said miniature robot on said fixation elements instead of said registration jig.

18. A method according to claim 16 wherein the position of said fixation elements is determined relative to the subject's head, and said miniature robot is then mounted with its base directly on said fixation elements, such that the position of said miniature robot is defined relative to said subject's head.

19. A method according to claim 16 wherein the position of said registration jig while it is mounted on said miniature robot is determined using said scanner, such that the position of said robot relative to said subject's head is defined.

20. A method according to claim 16 further comprising: providing a targeting guide supported by said miniature robot to direct a surgical tool, wherein said neurosurgical procedure delineates at least one entry point on the subject's head and at least one target point within the subject's head; adjusting said miniature robot to align said targeting guide to direct said surgical tool from said entry point towards said target point.

21. A method according to claim 16 wherein said registration procedure also matches a plurality of fiducial markers configured to be mounted on subject's head wherein said step of scanning at least part of the subject's head includes scanning locations of said fiducial markers, and wherein said registration procedure matches said locations of said fiducial markers with locations of said fiducial markers obtained from said preoperatively generated three dimensional image set.

22. A system according to claim 21, further comprising: providing a fiducial registration jig; and
attaching it in a predefined manner to at least some of said fiducial markers,
wherein said surface scan of at least part of the subject's head includes a scan of said fiducial registration jig, and
wherein said location of said fiducial markers is determined from a location of said fiducial registration jig.

23. A method according to claim 21 and wherein at least one of said at least one fiducial marker is a bone screw configured to be attached to the subject's head.

24. A method according to claim 16 and wherein said miniature robot is mounted in a fixed position relative to said fiducial markers.

25. A method according to claim 16 wherein said surface scan of at least part of the subject's head comprises a plurality of landmark features of said subject's head, and said registration procedure matches said landmark features to corresponding landmark features obtained from said preoperatively generated three dimensional image set.

26. A method according to claim 16 and wherein at least one of said registration jig and said miniature robot is mounted on either of a head immobilization clamp and a fixed stand disposed near the subject's head.

27. A method according to claim 16, wherein said miniature robot has a working volume and range sufficiently small relative to the skull of said subject wherein a preliminary coarse positioning method must be used, the method further comprising:
disposing a video camera in a predetermined position relative to said three dimensional scanner; and
displaying a real-time image of the subject's head,
wherein information is provided to said video camera from said preoperative plan to show on said real-time image a virtual indication of an approximate position for placement of said miniature robot.

28. A method according to claim 27 wherein said preliminary coarse positioning method is mandated by the miniature robot small work volume.

29. A method according to claim 27 wherein said miniature robot has a working volume of the order of 15 $cm^3$.

30. A method according to claim 16 wherein said three dimensional scanner is an optical scanner such that said scanning at least part of the subject's head to generate a three dimensional intraoperative surface scan of the subject's head is optical scanning.

31. A method according to claim 16, wherein said tetrahedron has base angles sufficiently large such that all four planes of said tetrahedron can be seen from a wide range of scanning viewpoints.

* * * * *